United States Patent
Sahney et al.

(10) Patent No.: US 10,251,539 B2
(45) Date of Patent: *Apr. 9, 2019

(54) HYSTEROSCOPIC SYSTEM

(71) Applicant: COVIDIEN LP, Mansfield, MA (US)

(72) Inventors: Mira Sahney, Boston, MA (US); Cemal Shener-Irmakoglu, Woburn, MA (US)

(73) Assignee: COVIDIEN LP, Mansfield, MA (US)

( * ) Notice: Subject to any disclaimer, the term of this patent is extended or adjusted under 35 U.S.C. 154(b) by 612 days.

This patent is subject to a terminal disclaimer.

(21) Appl. No.: 14/846,198

(22) Filed: Sep. 4, 2015

(65) Prior Publication Data
US 2015/0374221 A1    Dec. 31, 2015

Related U.S. Application Data

(63) Continuation of application No. 12/892,355, filed on Sep. 28, 2010, now Pat. No. 9,155,454.

(51) Int. Cl.
A61B 1/303 (2006.01)
A61B 1/00 (2006.01)
A61B 17/42 (2006.01)
A61B 17/34 (2006.01)
A61B 1/018 (2006.01)
(Continued)

(52) U.S. Cl.
CPC .......... *A61B 1/303* (2013.01); *A61B 1/00135* (2013.01); *A61B 1/015* (2013.01); *A61B 1/018* (2013.01); *A61B 17/3421* (2013.01); *A61B 17/42* (2013.01); *A61B 1/307* (2013.01); *A61B 17/32002* (2013.01); *A61B 17/3205* (2013.01); *A61B 2017/320024* (2013.01); *A61B 2017/320028* (2013.01);
(Continued)

(58) Field of Classification Search
CPC ... A61B 1/00135; A61B 1/303; A61B 17/042; A61B 17/32002; A61B 1/0125; A61B 1/018; A61B 1/317
See application file for complete search history.

(56) References Cited

U.S. PATENT DOCUMENTS 1,585,934 A   5/1926  Muir
1,666,332 A   4/1928  Hirsch
(Continued)

FOREIGN PATENT DOCUMENTS

CN    1695546 A    11/2005
CN    101662993 A   3/2010
(Continued)

OTHER PUBLICATIONS

European examination report issued in corresponding EP application No. 11770261.3 dated Aug. 4, 2016.
(Continued)

*Primary Examiner* — Timothy J Neal
*Assistant Examiner* — Aaron B Fairchild

(57) ABSTRACT

A hysteroscopy system includes a scope having an internal channel, a sheath removably coupled to the scope, and an outflow channel. The sheath has a distal flange extending internally towards an outer surface of the scope. The outflow channel is formed between an inner surface of the sheath and an outer surface of the scope. The distal flange forms a distal end of the outflow channel and is generally located between the scope and the sheath.

7 Claims, 8 Drawing Sheets

(51) Int. Cl.
  *A61B 1/015*      (2006.01)
  *A61B 17/32*      (2006.01)
  *A61B 17/3205*    (2006.01)
  *A61B 1/307*      (2006.01)

(52) U.S. Cl.
  CPC ............ *A61B 2017/320052* (2013.01); *A61B 2017/4216* (2013.01); *A61B 2217/007* (2013.01)

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman |
| 4,146,405 A | 3/1979 | Timmer |
| 4,198,958 A | 4/1980 | Utsugi |
| 4,203,444 A | 5/1980 | Bonnell |
| 4,210,146 A | 7/1980 | Banko |
| 4,246,902 A | 1/1981 | Martinez |
| 4,247,180 A | 1/1981 | Norris |
| 4,258,721 A | 3/1981 | Parent |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt |
| 4,493,698 A | 1/1985 | Wang |
| 4,517,977 A | 5/1985 | Frost |
| 4,543,965 A | 10/1985 | Pack |
| 4,567,880 A | 2/1986 | Goodman |
| 4,589,414 A | 5/1986 | Yoshida |
| 4,601,284 A | 7/1986 | Arakawa |
| 4,601,290 A | 7/1986 | Effron |
| 4,606,330 A | 8/1986 | Bonnet |
| 4,630,598 A | 12/1986 | Bonnet |
| 4,644,952 A | 2/1987 | Patipa |
| 4,649,919 A | 3/1987 | Thimsen |
| 4,700,694 A | 10/1987 | Shishido |
| 4,706,656 A | 11/1987 | Kuboto |
| 4,718,291 A | 1/1988 | Wood |
| 4,737,142 A | 4/1988 | Heckele |
| 4,749,376 A | 6/1988 | Kensey |
| 4,756,309 A | 7/1988 | Sachse |
| 4,819,635 A | 4/1989 | Shapiro |
| 4,844,064 A | 7/1989 | Thimsen |
| 4,850,354 A | 7/1989 | McGurk-Burleson |
| 4,856,919 A | 8/1989 | Takeuchi |
| 4,867,157 A | 9/1989 | McGurk-Burleson |
| 4,924,851 A | 5/1990 | Ognier |
| 4,940,061 A | 7/1990 | Terwilliger |
| 4,950,278 A | 8/1990 | Sachse |
| 4,955,882 A | 9/1990 | Hakky |
| 4,986,827 A | 1/1991 | Akkas |
| 4,998,527 A | 3/1991 | Meyer |
| 4,998,914 A | 3/1991 | Wiest |
| 5,007,917 A | 4/1991 | Evans |
| 5,027,792 A | 7/1991 | Meyer |
| 5,037,386 A | 8/1991 | Marcus |
| 5,105,800 A | 4/1992 | Takahashi |
| 5,106,364 A | 4/1992 | Hayafuji |
| 5,112,299 A | 5/1992 | Pascaloff |
| 5,116,868 A | 5/1992 | Chen |
| 5,125,910 A | 6/1992 | Freitas |
| 5,133,713 A | 7/1992 | Huang |
| 5,152,744 A | 10/1992 | Krause |
| 5,158,553 A | 10/1992 | Berry |
| 5,163,433 A | 11/1992 | Kagawa |
| 5,169,397 A | 12/1992 | Sakashita |
| 5,176,677 A | 1/1993 | Wuchinich |
| 5,195,541 A | 3/1993 | Obenchain |
| 5,226,910 A | 7/1993 | Kajiyama |
| 5,244,459 A | 9/1993 | Hill |
| 5,254,117 A | 10/1993 | Rigby |
| 5,269,785 A | 12/1993 | Bonutti |
| 5,270,622 A | 12/1993 | Krause |
| 5,275,609 A | 1/1994 | Pingleton |
| 5,288,290 A | 2/1994 | Brody |
| 5,304,118 A | 4/1994 | Trese |
| 5,312,399 A | 5/1994 | Hakky |
| 5,312,425 A | 5/1994 | Evans |
| 5,312,430 A | 5/1994 | Rosenbluth |
| 5,320,091 A | 6/1994 | Grossi |
| 5,347,992 A | 9/1994 | Pearlman |
| 5,350,390 A | 9/1994 | Sher |
| 5,364,395 A | 11/1994 | West, Jr. |
| 5,374,253 A | 12/1994 | Burns, Sr. |
| 5,390,585 A | 2/1995 | Ryuh |
| 5,392,765 A | 2/1995 | Muller |
| 5,395,313 A | 3/1995 | Naves |
| 5,403,276 A | 4/1995 | Schechter |
| 5,409,013 A | 4/1995 | Clement |
| 5,409,453 A | 4/1995 | Lundquist |
| 5,411,513 A | 5/1995 | Ireland |
| 5,421,819 A | 6/1995 | Edwards |
| 5,425,376 A | 6/1995 | Banys |
| 5,429,601 A | 7/1995 | Conley |
| 5,435,805 A | 7/1995 | Edwards |
| 5,443,476 A | 8/1995 | Shapiro |
| 5,449,356 A | 9/1995 | Walbrink |
| 5,456,673 A | 10/1995 | Ziegler |
| 5,456,689 A | 10/1995 | Kresch |
| 5,483,951 A | 1/1996 | Frassica |
| 5,490,819 A | 2/1996 | Nicholas |
| 5,490,860 A | 2/1996 | Middle |
| 5,492,537 A | 2/1996 | Vancaillie |
| 5,498,258 A | 3/1996 | Hakky |
| 5,527,331 A | 6/1996 | Kresch |
| 5,549,541 A | 8/1996 | Muller |
| 5,556,378 A | 9/1996 | Storz |
| 5,563,481 A | 10/1996 | Krause |
| 5,569,164 A | 10/1996 | Lurz |
| 5,569,254 A | 10/1996 | Carlson |
| 5,569,284 A | 10/1996 | Young |
| 5,575,756 A | 11/1996 | Karasawa |
| 5,591,187 A | 1/1997 | Dekel |
| 5,601,583 A | 2/1997 | Donahue |
| 5,601,603 A | 2/1997 | Illi |
| 5,602,449 A | 2/1997 | Krause |
| 5,603,332 A | 2/1997 | O'Connor |
| 5,630,798 A | 5/1997 | Beiser |
| 5,649,547 A | 7/1997 | Ritchart |
| 5,669,927 A | 9/1997 | Boebel |
| 5,672,945 A | 9/1997 | Krause |
| 5,674,179 A | 10/1997 | Bonnet |
| 5,676,497 A | 10/1997 | Kim |
| 5,695,448 A | 12/1997 | Kimura |
| 5,702,420 A | 12/1997 | Sterling |
| 5,709,698 A | 1/1998 | Adams |
| 5,730,752 A | 3/1998 | Alden |
| 5,733,298 A | 3/1998 | Berman |
| 5,741,286 A | 4/1998 | Recuset |
| 5,741,287 A | 4/1998 | Alden |
| 5,749,885 A | 5/1998 | Sjostrom |
| 5,749,889 A | 5/1998 | Bacich |
| 5,759,185 A | 6/1998 | Grinberg |
| 5,772,634 A | 6/1998 | Atkinson |
| 5,775,333 A | 7/1998 | Burbank |
| 5,782,849 A | 7/1998 | Miller |
| 5,807,240 A | 9/1998 | Muller |

(56) References Cited

U.S. PATENT DOCUMENTS

| | | | |
|---|---|---|---|
| 5,807,282 A | 9/1998 | Fowler |
| 5,810,770 A | 9/1998 | Chin |
| 5,810,861 A | 9/1998 | Gaber |
| 5,814,009 A | 9/1998 | Wheatman |
| 5,833,643 A | 11/1998 | Ross |
| 5,840,060 A | 11/1998 | Beiser |
| 5,857,995 A | 1/1999 | Thomas |
| 5,873,886 A | 2/1999 | Larsen |
| 5,899,915 A | 5/1999 | Saadat |
| 5,911,699 A | 6/1999 | Anis |
| 5,911,722 A | 6/1999 | Adler |
| 5,913,867 A | 6/1999 | Dion |
| 5,916,229 A | 6/1999 | Evans |
| 5,925,055 A | 7/1999 | Adrian |
| 5,928,163 A | 7/1999 | Roberts |
| 5,944,668 A | 8/1999 | Vancaillie |
| 5,947,990 A | 9/1999 | Smith |
| 5,951,490 A | 9/1999 | Fowler |
| 5,956,130 A | 9/1999 | Vancaillie |
| 5,957,832 A | 9/1999 | Taylor |
| 6,001,116 A | 12/1999 | Heisler |
| 6,004,320 A | 12/1999 | Casscells |
| 6,007,513 A | 12/1999 | Anis |
| 6,024,751 A | 2/2000 | Lovato |
| 6,032,673 A | 3/2000 | Savage |
| 6,039,748 A | 3/2000 | Savage |
| 6,042,552 A | 3/2000 | Cornier |
| 6,068,641 A | 5/2000 | Varsseveld |
| 6,086,542 A | 7/2000 | Glowa |
| 6,090,094 A | 7/2000 | Clifford |
| 6,090,123 A | 7/2000 | Culp |
| 6,113,594 A | 9/2000 | Savage |
| 6,119,973 A | 9/2000 | Galloway |
| 6,120,147 A | 9/2000 | Vijfvinkel |
| 6,120,462 A | 9/2000 | Hibner |
| 6,132,448 A | 10/2000 | Perez |
| 6,149,633 A | 11/2000 | Maaskamp |
| 6,156,049 A | 12/2000 | Lovato |
| 6,159,160 A | 12/2000 | Hsei |
| 6,159,209 A | 12/2000 | Hakky |
| 6,203,518 B1 | 3/2001 | Anis |
| 6,217,543 B1 | 4/2001 | Anis |
| 6,224,603 B1 | 5/2001 | Marino |
| 6,244,228 B1 | 6/2001 | Kuhn |
| 6,258,111 B1 | 7/2001 | Ross |
| 6,277,096 B1 | 8/2001 | Cortella |
| 6,315,714 B1 | 11/2001 | Akiba |
| 6,358,200 B1 | 3/2002 | Grossi |
| 6,358,263 B2 | 3/2002 | Mark |
| 6,359,200 B1 | 3/2002 | Day |
| 6,402,701 B1 | 6/2002 | Kaplan |
| 6,428,486 B2 | 8/2002 | Ritchart |
| 6,443,947 B1 * | 9/2002 | Marko ............... A61B 18/08 606/28 |
| 6,471,639 B2 | 10/2002 | Rudischhauser |
| 6,494,892 B1 | 12/2002 | Ireland |
| 6,585,708 B1 | 7/2003 | Maaskamp |
| 6,610,066 B2 | 8/2003 | Dinger |
| 6,626,827 B1 | 9/2003 | Felix |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel |
| 6,837,847 B2 | 1/2005 | Ewers |
| 7,025,720 B2 | 4/2006 | Boebel |
| 7,025,732 B2 | 4/2006 | Thompson |
| 7,150,713 B2 | 12/2006 | Shener |
| 7,226,459 B2 | 6/2007 | Cesarini |
| 7,249,602 B1 | 7/2007 | Emanuel |
| 7,510,563 B2 | 3/2009 | Cesarini |
| 7,763,033 B2 | 7/2010 | Gruber |
| 7,922,737 B1 | 4/2011 | Cesarini |
| 8,061,359 B2 | 11/2011 | Emanuel |
| 8,062,214 B2 | 11/2011 | Shener |
| 8,419,626 B2 | 4/2013 | Shener-Irmakoglu |
| 8,663,264 B2 | 3/2014 | Cesarini |
| 8,678,999 B2 | 3/2014 | Isaacson |
| 8,852,085 B2 | 10/2014 | Shener-Irmakoglu |
| 8,893,722 B2 | 11/2014 | Emanuel |
| 8,932,208 B2 | 1/2015 | Kendale |
| 8,951,274 B2 | 2/2015 | Adams |
| 9,060,800 B1 | 6/2015 | Cesarini |
| 9,060,801 B1 | 6/2015 | Cesarini |
| 9,066,745 B2 | 6/2015 | Cesarini |
| 9,072,431 B2 | 7/2015 | Adams |
| 9,089,358 B2 | 7/2015 | Emanuel |
| 9,125,550 B2 | 9/2015 | Shener-Irmakoglu |
| 9,155,454 B2 | 10/2015 | Sahney |
| 2001/0039963 A1 | 11/2001 | Spear |
| 2001/0047183 A1 | 11/2001 | Privitera |
| 2002/0058859 A1 | 5/2002 | Brommersma |
| 2002/0165427 A1 | 11/2002 | Yachia |
| 2003/0050603 A1 | 3/2003 | Todd |
| 2003/0050638 A1 | 3/2003 | Yachia |
| 2003/0078609 A1 | 4/2003 | Finlay |
| 2003/0114875 A1 | 6/2003 | Sjostrom |
| 2004/0204671 A1 | 10/2004 | Stubbs |
| 2005/0043690 A1 | 2/2005 | Todd |
| 2005/0085692 A1 | 4/2005 | Kiehn |
| 2005/0234298 A1 * | 10/2005 | Kucklick ............ A61B 1/00135 600/156 |
| 2006/0036132 A1 | 2/2006 | Renner |
| 2006/0047185 A1 | 3/2006 | Shener et al. |
| 2006/0241586 A1 | 10/2006 | Wilk |
| 2007/0073101 A1 | 3/2007 | Queyroux et al. |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams |
| 2008/0097469 A1 | 4/2008 | Gruber |
| 2008/0097470 A1 | 4/2008 | Gruber |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2009/0012362 A1 | 1/2009 | Kucklick |
| 2009/0082628 A1 | 3/2009 | Kucklick et al. |
| 2009/0270812 A1 | 10/2009 | Litscher |
| 2009/0270895 A1 | 10/2009 | Churchill |
| 2009/0270896 A1 | 10/2009 | Sullivan |
| 2009/0270897 A1 | 10/2009 | Adams |
| 2009/0270898 A1 | 10/2009 | Chin |
| 2010/0087798 A1 | 4/2010 | Adams |
| 2010/0152647 A1 | 6/2010 | Shener |
| 2011/0166419 A1 | 7/2011 | Reif |
| 2012/0078038 A1 | 3/2012 | Sahney |
| 2013/0131452 A1 | 5/2013 | Kuroda |
| 2014/0031834 A1 | 1/2014 | Germain |

FOREIGN PATENT DOCUMENTS

| | | |
|---|---|---|
| DE | 3339322 A1 | 5/1984 |
| DE | 3206381 C2 | 7/1986 |
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 5/1997 |
| EP | 1681022 A1 | 7/2006 |
| GB | 2093353 A | 9/1982 |

(56) References Cited

FOREIGN PATENT DOCUMENTS

| | | |
|---|---|---|
| GB | 2311468 A | 10/1997 |
| JP | 2001-75416 | 5/1989 |
| JP | 2002 529185 A | 9/2002 |
| JP | 2002 538889 A | 11/2002 |
| JP | 2003 245247 A | 9/2003 |
| JP | 2005319086 A | 11/2005 |
| NL | 1006944 C2 | 3/1999 |
| WO | WO 1981/01648 A1 | 6/1981 |
| WO | WO 1992/11816 A2 | 7/1992 |
| WO | WO 1993/07821 A1 | 4/1993 |
| WO | WO 1993/15664 A1 | 8/1993 |
| WO | WO 1994/26181 A1 | 11/1994 |
| WO | WO 1995/05777 A1 | 3/1995 |
| WO | WO 1995/10981 A1 | 4/1995 |
| WO | WO 1995/10982 A1 | 4/1995 |
| WO | WO 1995/22935 A1 | 8/1995 |
| WO | WO 1995/30377 A1 | 11/1995 |
| WO | WO 1996/11638 A1 | 4/1996 |
| WO | WO 1996/26676 A1 | 9/1996 |
| WO | WO 1997/09922 A1 | 3/1997 |
| WO | WO 1997/17027 A1 | 5/1997 |
| WO | WO 1997/19642 A1 | 6/1997 |
| WO | WO 1997/24071 A1 | 7/1997 |
| WO | WO 1997/34534 A1 | 9/1997 |
| WO | WO 1997/35522 A1 | 10/1997 |
| WO | WO 1998/09569 A1 | 3/1998 |
| WO | WO 1998/10707 A1 | 3/1998 |
| WO | WO 1998/46147 A1 | 10/1998 |
| WO | WO 1999/03407 A1 | 1/1999 |
| WO | WO 1999/03409 A1 | 1/1999 |
| WO | WO 1999/07295 A1 | 2/1999 |
| WO | WO 1999/11184 A1 | 3/1999 |
| WO | WO 1999/39648 A1 | 8/1999 |
| WO | WO 1999/44506 A1 | 9/1999 |
| WO | WO 1999/60935 A1 | 12/1999 |
| WO | WO 2000/12010 A1 | 3/2000 |
| WO | WO 2000/28890 A1 | 5/2000 |
| WO | WO 2000/33743 A1 | 6/2000 |
| WO | WO 2000/44295 A1 | 8/2000 |
| WO | WO 2000/47116 A1 | 8/2000 |
| WO | WO 2000/57797 A1 | 10/2000 |
| WO | WO 2001/35831 A1 | 5/2001 |
| WO | WO 2001/58368 A1 | 8/2001 |
| WO | WO 2001/95810 A2 | 12/2001 |
| WO | WO 2002/069808 A2 | 9/2002 |
| WO | WO 2003/022164 A1 | 3/2003 |
| WO | WO 2003/077767 A1 | 9/2003 |
| WO | WO 2005/060842 A1 | 7/2005 |
| WO | WO 2005/096963 A2 | 10/2005 |
| WO | WO 2006/105283 A2 | 10/2006 |
| WO | WO 2006/121968 A2 | 11/2006 |
| WO | WO 2006/121970 A2 | 11/2006 |
| WO | WO 2007/044833 A2 | 4/2007 |
| WO | WO 2012/044705 A1 | 4/2012 |

OTHER PUBLICATIONS

Notification of Reason for Refusal issued in corresponding Korean application No. 10-2013-7008294 dated Dec. 14, 2017.
Chinese Office Action for Chinese Application No. 201180046921.6, dated Dec. 15, 2015, 3 pages, with English language translation.
Inquiry Made in Course of Substantive Examination for Russian Patent Application No. 2013119298/14(028553) dated Sep. 29, 2015, 5 pages, with English language translation.
ACMI Corporation, "Dolphin II Hysteroscopic Fluid Management Systems," ACMI Corporation, 2002 (1 page).
ACMI Corporation, "Dolphin II and Disten-U-Flo Fluid Management Systems for Hysteroscopy", ACMI Corporation, 2002 (1 page).
Bacsko "Uterine Surgery by Operative Hysteroscopy", European Journal of Obstetrics & Gynecology and Reproductive Biology, vol. 71, pp. 219-222, 1997 (4 pages).
Baggish et al., "Diagnostic and Operative Hysterectomy," Mosby, pp. 97-105, 123-125, 127-132, 353-355, and 394-398, 1999 (27 pages).
Chinese Office Action for Chinese Application No. 201180046921.6, dated Dec. 23, 2014, 29 pages, with English language translation.
C.R. Bard, Inc, "The HydroFlex HD System" (1 page).
Cravello et al., "Hysteroscopic Resection of Fibroids: Results with a 6-Year Follow-up Period", Journal of Gynecologic Surgery, vol. 15, No. 1, 1-5 1999 (5 pages).
Defendant Hologic Inc.'s Preliminary, Non-Binding List of Asserted Prior Art References, dated Feb. 8, 2012, in *Smith & Nephew, Inc. v. Hologic, Inc.*, Civil Action Nos. 11-12064-RWZ and 10- 10951-RWZ, U.S. District Court for the District of Massachusetts (7 pages).
Dictionary definition of reciprocate, Merrian-Webster Dictionary, on-line edition, retrieved Mar. 20, 2013 (1 page).
Dictionary definition of rotate, Merriam-Webster Dictionary, on-line edition, retrieved Mar. 20, 2013 (1 page).
Dictionary definition of translate, Merriam-Webster Dictionary, on-line edition, retrieved Mar. 20, 2013 (1 page).
Drews et al., "Surgical Approach to Myomas: Laparoscopy and Hysteroscopy", Seminars in Reproductive Endocrinology, vol. 10, No. 4, pp. 367-377, 1992 (11 pages).
Dumesic et al., "A New Approach to Hysteroscopic Cannulation of the Fallopian Tube", Journal of Gynecologic Surgery, vol. 7, No. 1, pp. 7-9, 1991 (3 pages).
Emanuel et al., "Long-term Results of Hysteroscopic Myomectomy for Abnormal Uterine Bleeding", Obstetrics & Gynecoogy, vol. 93, No. 5, Part I, pp. 743-748, 1999 (6 pages).
European Patent Application No. 05 786 521.4-2305, Examination Report dated Apr. 21, 2010 (4 pages).
European Patent Application No. 05 786 521.4-2305, Examination Report dated Sep. 26, 2012 (5 pages).
European Patent Application No. 11 770 261.3-1657, Examination Report dated Feb. 11, 2014 (4 pages).
Exhibit P to Hologic's Opposition to Smith & Nephew's Motion for Preliminary Injunction, Redacted, filed Dec. 30, 2011, in *Smith & Nephew, Inc. v. Hologic, Inc.*, Civil Action No. 11-12064-RWZ, U.S. District Court for the District of Massachusetts (99 pages).
First Office Action for Japanese Patent Application No. 213-531779 dated May 18, 2015, with English translation, 6 pages.
Franchini et al., "Endometrial resection: a diagnostic tool in post-menopausal women", Gynecological Endoscopy, 8, pp. 111-114, 1999 (5 pages).
"From Distention to Deficit Monitoring Taking the All-in-One Approach", W.O.M. World of Medicine (1 page).
Gerber et al., "The Endoscapel: A new endoscopic instrument for supracervical hysterectomy and morcellation of masses; clinical evaluation", European Journal of Obstetrics & Gynecology and Reproductive Biology, 86, p. S12, 1999 (1 page).
Gynecare "Motor Drive Unit" Instructions for Use (3 pages).
Gynecare X-Tract, "Tissue Morcellator", Instructions for Use (3 pages).
Gynecare, "Fluid Management System" Instructions for Use (26 pages).
Gynescope Corporation "Laser Fiber Director", Advertisement, Journal of Gynecologic Surgery, vol. 6, No. 1, 1990 (2 pages).
Hess et al., "Textbook of Bilio-Pancreatic Disease", vol. III, Piccin, e.g. Fig 6.5.1, pp. 1584-1586, 1997 (5 pages).
Hologic's Opposition to Smith & Nephew's Motion for Preliminary Injunction, Redacted, filed Dec. 30, 2011, in *Smith & Nephew, Inc. v. Hologic, Inc.*, Civil Action No. 11- 12064-RWZ, U.S. District Court for the District of Massachusetts (26 pages).
"HysteRo-Purator 1143-1 Technical Data" WISAP (2 pages).
International Application No. PCT/US2005/029807, International Preliminary Report on Patentability dated Feb. 28, 2007 (9 pages).
International Application No. PCT/US2005/029807, International Search Report dated Jun. 13, 2006 (5 pages).
International Application No. PCT/US2011/053753, International Preliminary Report on Patentability dated Apr. 2, 2013 (7 pages).
International Application No. PCT/US2011/053753, International Search Report dated Dec. 20, 2011 (4 pages).
Japanese Patent Application No. 2007-530014, Translation of Office Action dated Feb. 15, 2011 (10 pages).

(56) References Cited

OTHER PUBLICATIONS

Karl Storz "Pilot a Course to Successful Outcomes", Intermetro Industries Corporation, 2001 (2 pages).
Karl Storz "Uterine Resectoscopes for Endometrial Ablation and Resection", Advertisement, Journal of Gynecologic Surgery, vol. 6, No. 1, 1990 (3 pages).
Karl Storz, Advertisement, Journal of Gynecologic Surgery, vol. 5, No. 4, 1989 (3 pages).
Lin et al. "Clinical Applications of a New Fujinon Operating Fiberoptic Hysteroscope", Journal of Gynecologic Surgery, vol. 6, No. 2, pp. 81-87, 1990 (7 pages).
Mettler et al., "Pelviscopic uterine surgery" Surgical Endoscopy, 6, pp. 23-31, 1992 (9 pages).
Neis et al., "Hysteroscopy: Textbook and Atlas", Thieme Medical Publishers, pp. 91-103, 1994 (13 pages).
Nisolle et al., "Endometrial ablation with the Nd-YAG laser in dysfunctional bleeding" Minimally Invasive Therapy, vol. 1, pp. 35-39, 1991 (5 pages).
Olympus Product Catalogue: Part No. A2461—OP Nephroscope, Sep. 1991 (3 pages).
Office Action in Chinese Patent Application No. 201180046921.6, dated Aug. 4, 2015, 13 pages.
Park et al., "Endoscopic Management of Uterine Myoma", Yonsei Medical Journal, vol. 40, No. 6, pp. 583-588, 1999 (6 pages).
Patent Examination Report No. 1 for Australian Patent Application No. 2011308834 dated Jun. 11, 2015, 3 pages.
Reexamination No. 95/001,933, Action Closing Prosecution mailed Sep. 19, 2013 (41 pages).
Reexamination No. 95/001,933, Appendices 14-28 to Request for Inter Partes Reexamination of U.S. Pat. No. 7,226,459, Claim Charts for Various Claims in view of Various References (436 pages).
Reexamination No. 95/001,933, Appendix 2 to Request for Inter Partes Reexamination of U.S. Pat. No. 7,226,459, Memorandum of Decision dated Apr. 21, 2011, in *Smith & Nephew, Inc.* v. *Interlace Medical, Inc.*, Civil Action No. 10-10951-RWZ, U.S. District Court for the District of Massachusetts (14 pages).
Reexamination No. 95/001,933, Appendix 6 to Request for Inter Partes Reexamination of U.S. Pat. No. 7,226,459, Opening Markman Brief of Plaintiff Smith & Nephew, Inc. dated Oct. 13, 2010, in *Smith & Nephew, Inc.* v. *Interlace Medical, Inc.*, Civil Action No. 10-10951-RWZ, U.S. District Court for the District of Massachusetts (23 pages).
Reexamination No. 95/001,933, Appendix 7 to Request for Inter Partes Reexamination of U.S. Pat. No. 7,226,459, Defendant Interlace Medical, Inc's Responsive Markman Brief (Redacted) dated Oct. 27, 2010, in *Smith & Nephew, Inc.* v. *Interlace Medical, Inc.*, Civil Action No. 10-10951-RWZ, U.S. District Court for the District of Massachusetts (26 pages).
Reexamination No. 95/001,933, Appendix 8 to Request for Inter Partes Reexamination of U.S. Pat. No. 7,226,459, Plaintiff Smith & Nephew, Inc.'s Reply in Support of Markman Brief dated Nov. 3, 2010, in *Smith & Nephew, Inc.* v. *Interlace Medical, Inc.*, Civil Action No. 10-10951-RWZ, U.S. District Court for the District of Massachusetts (8 pages).
Reexamination No. 95/001,933, Examiner's Answer dated Mar. 25, 2015 (3 pages).
Reexamination No. 95/001,933, Executed Expert Declaration of Hal Walbrink in support of Request for Inter Partes Reexamination of U.S. Pat. No. 7,226,459, Executed Mar. 9, 2012 (42 pages).
Reexamination No. 95/001,933, First Office Action dated Jun. 5, 2012 (37 pages).
Reexamination No. 95/001,933, Litigation Search Report CRU 3999 dated Mar. 29, 2012 (24 pages).
Reexamination No. 95/001,933, Order Granting Request for Reexamination dated Jun. 5, 2012 (29 pages).
Reexamination No. 95/001,933, Patent Owner's Apr. 14, 2014 Appeal Brief (334 pages).
Reexamination No. 95/001,933, Patent Owner's Feb. 13, 2014 Notice of Appeal (2 pages).
Reexamination No. 95/001,933, Patent Owner's Aug. 6, 2012 Response to First Office Action dated Jun. 5, 2012 (156 pages).
Reexamination No. 95/001,933, Patent Owner's Jun. 3, 2013 Response to Second Office Action dated Apr. 1, 2013 (37 pages).
Reexamination No. 95/001,933, Patent Owner's Oct. 21, 2013 Response to Action Closing Prosecution dated Sep. 19, 2013 (180 pages).
Reexamination No. 95/001,933, Right of Appeal Notice mailed Jan. 14, 2014 (58 pages).
Reexamination No. 95/001,933, Second Office Action dated Apr. 1, 2013 (56 pages).
Reexamination No. 95/001,933, Third Party's Dec. 19, 2012 Response to Notification of Defective Paper and Comments on First Office Action dated Jun. 5, 2012 (38 pages).
Reexamination No. 95/001,933, Third Party's Jul. 3, 2013 Comments on Second Office Action dated Apr. 1, 2013 (62 pages).
Reexamination No. 95/001,933, Third Party's Mar. 12, 2012 Request for Inter Partes Reexamination of U.S. Pat. No. 7,226,459 (130 pages).
Reexamination No. 95/001,933, Third Party's May 14, 2014 Respondent's Brief (303 pages).
Reexamination No. 95/001,933, Third Party's Nov. 20, 2013 Comments on Action Closing Prosecution mailed Sep. 19, 2013 (38 pages).
Reexamination No. 95/001,933, Third Party's Sep. 5, 2012 Comments on First Office Action dated Jun. 5, 2012 (210 pages).
Reexamination No. 95/001,955, Appendix 19 to Request for Inter Partes Reexamination of U.S. Pat. No. 8,061,359, Opening Claim Construction Brief of Defendant Hologic, Inc., dated Feb. 24, 2012, in *Smith & Nephew, Inc.* v. *Hologic, Inc.*, Civil Action No. 11-12064-RWZ, U.S. District Court for the District of Massachusetts (24 pages).
Reexamination No. 95/001,955, Appendix 20 to Request for Inter Partes Reexamination of U.S. Pat. No. 8,061,359, Opening Markman Brief of Plaintiff Smith & Nephew, Inc., dated Feb. 24, 2012, in *Smith & Nephew, Inc.* v. *Hologic, Inc.*, Civil Action No. 11-12064-RWZ, U.S. District Court for the District of Massachusetts (24 pages).
Reexamination No. 95/001,955, Appendix 28 to Request for Inter Partes Reexamination of U.S. Pat. No. 8,061,359, Claim chart for anticipation of claims 1-8 based on U.S. Pat. No. 5,456,689 to Kresch (4 pages).
Reexamination No. 95/001,955, Appendix 29 to Request for Inter Partes Reexamination of U.S. Pat. No. 8,061,359, Claim chart for anticipation of claims 1-8 based on U.S. Pat. No. 6,032,673 to Savage (13 pages).
Reexamination No. 95/001,955, Appendix 30 to Request for Inter Partes Reexamination of U.S. Pat. No. 8,061,359, Claim chart for anticipation of claims 1-8 based on U.S. Pat. No. 3,945,375 to Banko (4 pages).
Reexamination No. 95/001,955, Decision Denying Petition dated Sep. 28, 2012 (5 pages).
Reexamination No. 95/001,955, Executed Expert Declaration of Dr. Henry A. Dominicis in support of Request for Inter Partes Reexamination of U.S. Pat. No. 8,061,359, Executed Apr. 1, 2012 (150 pages).
Reexamination No. 95/001,955, Executed Expert Declaration of Hal Walbrink in support of Request for Inter Partes Reexamination of U.S. Pat. No. 8,061,359, Executed Apr. 2, 2012 (22 pages).
Reexamination No. 95/001,955, Litigation Search Report CRU 3999 dated Apr. 3, 2012 (33 pages).
Reexamination No. 95/001,955, Order Denying Request for Inter Partes Reexamination mailed Jun. 4, 2012 (35 pages).
Reexamination No. 95/001,955, Request for Inter Partes Reexamination of U.S. Pat. No. 8,061,359, filed Apr. 2, 2012 (265 pages).
Reexamination No. 95/001,955, Request for Reconsideration of Third Party Requestor's Petition for Reexamination mailed Jul. 3, 2012 (32 pages).
Reexamination No. 95/002,058, Executed Expert Declaration of Dr. Henry A. Dominicis in support of Request for Inter Partes Reexamination of U.S. Pat. No. 8,061,359, Executed Jul. 24, 2012 (101 pages).

(56) References Cited

OTHER PUBLICATIONS

Reexamination No. 95/002,058, First Action Closing Prosecution mailed Aug. 9, 2013 (34 pages).
Reexamination No. 95/002,058, First Office Action dated Sep. 19, 2012 (37 pages).
Reexamination No. 95/002,058, Litigation Search Report CRU 3999 dated Aug. 13, 2012 (29 pages).
Reexamination No. 95/002,058, Patent Owner's Mar. 5, 2015 Notice of Appeal (2 pages).
Reexamination No. 95/002,058, Patent Owner's Jan. 22, 2013 Response to First Office Action dated Sep. 19, 2012 (379 pages).
Reexamination No. 95/002,058, Patent Owner's Mar. 24, 2014 Response to Second Office Action dated Jan. 24, 2014 (55 pages).
Reexamination No. 95/002,058, Patent Owner's Sep. 29, 2014 Response to Second Action Closing Prosecution mailed Aug. 27, 2014 (12 pages).
Reexamination No. 95/002,058, Patent Owner's Sep. 9, 2013 Response to First Action Closing Prosecution dated Aug. 9, 2013 (159 pages).
Reexamination No. 95/002,058, Reexam Order dated Sep. 19, 2012 (54 pages).
Reexamination No. 95/002,058, Right of Appeal Notice mailed Feb. 4, 2015 (35 pages).
Reexamination No. 95/002,058, Second Action Closing Prosecution mailed Aug. 27, 2014 (35 pages).
Reexamination No. 95/002,058, Second Office Action dated Jan. 24, 2014 (31 pages).
Reexamination No. 95/002,058, Third Party's Apr. 23, 2014 Comments on Second Office Action mailed Jan. 24, 2014 (117 pages).
Reexamination No. 95/002,058, Third Party's Feb. 21, 2013 Comments on First Office Action mailed Sep. 19, 2012 (771 pages).
Reexamination No. 95/002,058, Third Party's Jul. 24, 2012 Request for Inter Partes Reexamination of U.S. Pat. No. 8,061,359 (1050 pages).
Reexamination No. 95/002,058, Third Party's Oct. 19, 2012 Request for Reconsideration of Certain Decisions Regarding Third Party Requestor's Request for Reexamination of U.S. Pat. No. 8,061,359 (19 pages).
Reexamination No. 95/002,058, Third Party's Oct. 29, 2014 Comments on Second Action Closing Prosecution mailed Aug. 27, 2014 (31 pages).
Reexamination No. 95/002,058, Third Party's Oct. 9, 2013 Comments on First Action Closing Prosecution mailed Aug. 9, 2013 (25 pages).
Reference AQ "Fishing Reel produced and sold by Shimano of Japan in to the U.S. prior to Oct. 26, 2001," as cited in the IDS filed Oct. 17, 2005 in the prosecution file history of U.S. Appl. No. 09/983,810 (7 pages).
Richard Wolf "'Morce—Power 2306' Electronic Morcellator" (2 pages).
Richard Wolf "The Fluid Manager" (2 pages).
Sheth, "Fiberoptic Light for Oophorectomy at Vaginal Hysterectomy", Journal of Gynecologic Surgery, vol. 14, No. 3, pp. 119-122, 1998 (4 pages).

Substantive Examination Report in the corresponding Patent Application No. MX/a/2013/003535, dated Aug. 20, 2015, 4 pages.
Sugimoto "A Color Atlas of Hysteroscopy" Springer-Verlag Tokyo, 1999 (17 pages).
U.S. Appl. No. 09/486,977, Office Action dated Sep. 7, 2005 (7 pages).
U.S. Appl. No. 11/780,759, Applicant's Mar. 31, 2011 Response to Office Action dated Jan. 5, 2010 (15 pages).
U.S. Appl. No. 11/780,759, Applicant's Oct. 25, 2010 Response to Office Action dated Jul. 26, 2010 (13 pages).
U.S. Appl. No. 11/780,759, Office Action dated Jan. 5, 2011 (7 pages).
U.S. Appl. No. 11/780,759, Office Action dated Jul. 22, 2010 (5 pages).
U.S. Appl. No. 11/780,759, Office Action dated Jul. 26, 2010 (7 pages).
U.S. Appl. No. 11/929,938, Office Action dated Jan. 5, 2011 (10 pages).
U.S. Appl. No. 11/929,938, Office Action dated Jul. 30, 2010 (10 pages).
U.S. Appl. No. 11/929,940, Advisory Action dated Sep. 10, 2010 (3 pages).
U.S. Appl. No. 11/929,940, Office Action dated Dec. 30, 2009 (9 pages).
U.S. Appl. No. 11/929,940, Office Action dated Jul. 1, 2010 (12 pages).
Valle "Hysteroscopic Removal of Submucous Leiomyomas", Journal of Gynecologic Surgery, vol. 6, No. 1, pp. 89-96, 1990 (9 pages).
Weck "A Direct Path to Diagnostic and Operative Control: The Weck-Baggish Hysteroscopy System" Advertisement, Journal of Gynecologic Surgery, vol. 7, No. 1, 1991 (2 pages).
Williamson et al., Editorial 1 "Complications of hysteroscopic treatments of menorrhagia", British Journal of Anesthesia, vol. 77, No. 3, pp. 305-308, 1996 (4 pages).
Reexamination No. 95/002,058, Patent Owner's May 5, 2015 Appeal Brief (47 pages).
Reexamination No. 95/002,058, Third Party's Jun. 5, 2015 Respondent Brief (21 pages).
Reexamination No. 95/002,058, Patent Owner's Jul. 1, 2015 Corrected Appeal Brief (47 pages).
Reexamination No. 95/002,058, Third Party's Jul. 24, 2015 Resubmitted Respondent Brief (21 pages).
Reexamination No. 95/002,058, Examiner's Answer dated Sep. 17, 2015 (3 pages).
Reexamination No. 95/002,058, Patent Owner's Oct. 19, 2015 Rebuttal Brief (25 pages).
Reexamination No. 95/001,933, Patent Owner's Apr. 24, 2015 Rebuttal Brief (8 pages).
Notification on Results of Patentability Examination for Russian Application No. 2013119298/14(028553), dated Jan. 14, 2016, 8 pages, with English language translation.
Notification of Second Office Action issued in corresponding Chinese Application No. 201611020781.6 dated Jun. 1, 2018, 18 pages with English translation.

* cited by examiner

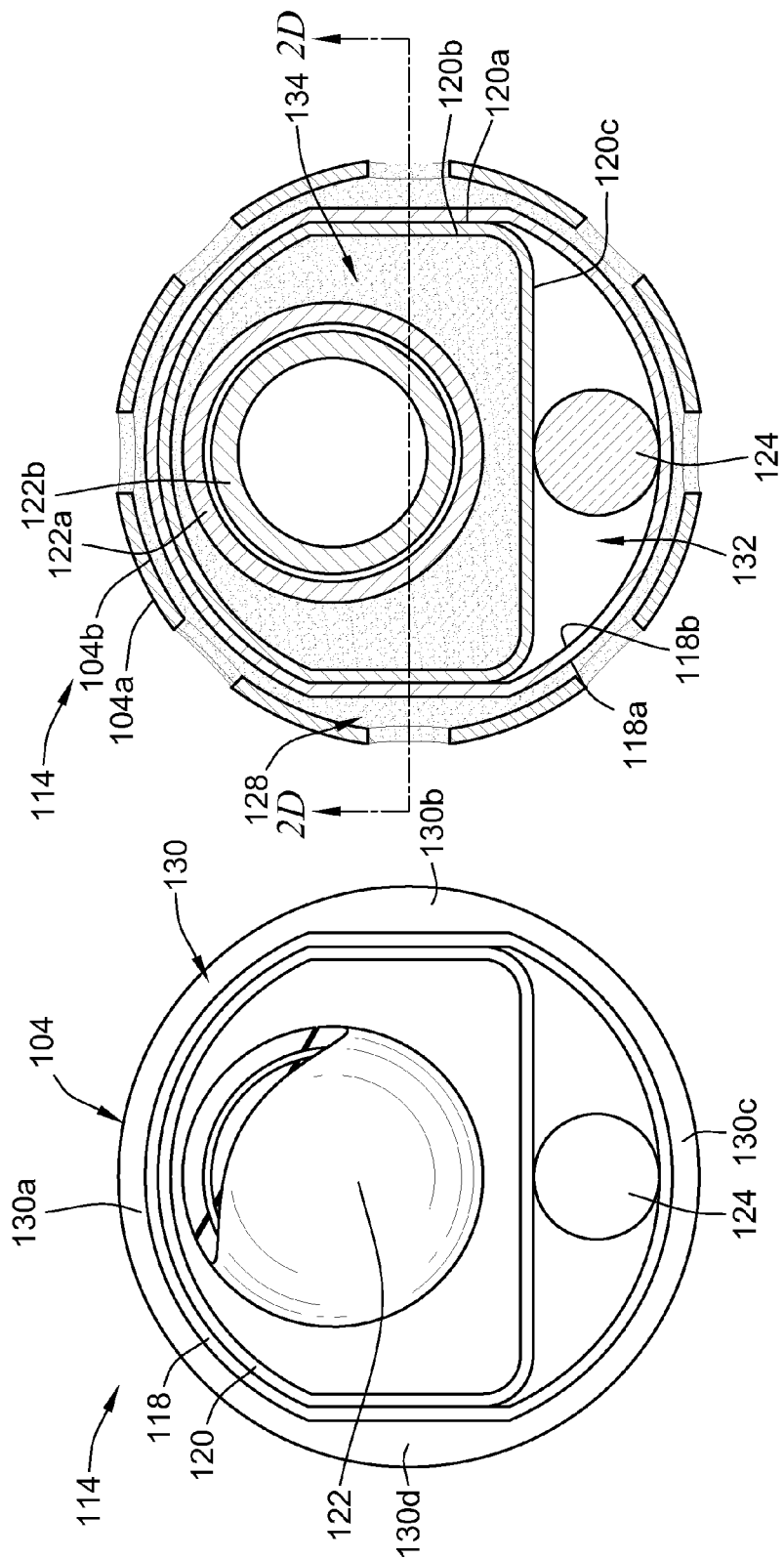

HYSTEROSCOPIC SYSTEM

CROSS-REFERENCE TO RELATED APPLICATION

The present application is a continuation of U.S. patent application Ser. No. 12/892,355, filed Sep. 28, 2010, now allowed, which is hereby incorporated by reference herein in its entirety.

FIELD OF THE INVENTION

The present invention relates generally to hysteroscopy systems, and, more particularly, to a hysteroscopy system having a small size for use in an office setting.

BACKGROUND OF THE INVENTION

Hysteroscopy refers generally to the inspection of a uterine cavity using a hysteroscope with access through the cervix. As such, hysteroscopy allows diagnosis of intrauterine pathology and, furthermore, can be used for surgical intervention. The hysteroscope typically includes a scope and a sheath.

One problem associated with some current hysteroscopy systems is that they must be used in an operating room setting with the patient being under some type of anesthesia. Anesthesia is required in particular because the size of current hysteroscopes is large and, as such, they can cause discomfort and pain to the patient. For example, a typical hysteroscope may have an outermost diameter of about 9 millimeters. Such hysteroscopes include a scope having a diameter of about 8 millimeters and a sheath having a diameter of about 9 millimeters. In comparison, scientific literature on the subject agrees that hysteroscopy can be performed using a vaginoscopic approach, which can be performed in an office setting, only when the outermost diameter of the hysteroscope is about 6 millimeters or less.

Another problem associated with current scopes is that they typically include a blunt flange at the scope distal end. The flange extends outwardly from the scope and make it difficult, if not impossible, to use the scope without the sheath and/or without an obturator. Accordingly, the size of some current hysteroscopes is limited to the size of the scope and the sheath, .e.g., a diameter of 9 millimeters.

What is needed, therefore, is a hysteroscope system for an office setting that addresses the above-stated and other problems.

SUMMARY OF THE INVENTION

According to one aspect of the present invention, a hysteroscopy system is directed to performing a medical procedure in an office setting. The hysteroscopy system includes a scope having an outer surface, an internal channel defined by an inner surface, and a distal end. A sheath is removably coupled to the scope and has a tip at which a distal flange extends internally towards the outer surface of the scope. The sheath also has an inner surface and a plurality of outflow holes near the distal flange. An outflow channel is formed between the inner surface of the sheath and the outer surface of the scope, the distal flange forming a distal end of the outflow channel. An operative channel is formed within the internal channel of the scope for receiving at least one of a surgical tool and an inflow fluid, and a visualization channel is formed adjacent to the operative channel for receiving a visualization device.

According to yet another aspect of the invention, a hysteroscopy system for a medical procedure includes a scope in the form of an elongated tubular member having an outer surface and an internal surface. The internal surface of the scope defines an internal channel of the scope. A sheath is in the form of an elongated tubular member removably coupled to the scope, the sheath having an outer surface and an internal surface. The sheath has a flange extending internally towards the outer surface of the scope at a distal end of the sheath. An operative member is located within the internal channel of the scope and is in the form of an elongated D-shape tubular member. The operative member has an outer surface and an internal surface, the outer surface being spaced away from the internal surface of the scope to form a visualization channel.

According to yet another aspect of the invention, a hysteroscopy system includes a scope having an outer surface and an internal channel, and a sheath removably coupled to the scope. The sheath has an inner surface and a distal flange, the distal flange extending internally towards the outer surface of the scope. An outflow channel is formed between the inner surface of the sheath and the outer surface of the scope, the distal flange forming a distal end of the outflow channel between the scope and the sheath.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 2B is an enlarged side view of the distal end of the hysteroscope system.

FIG. 2C is an enlarged cross-sectional end view of the distal end of the hysteroscope system.

Figure 1:
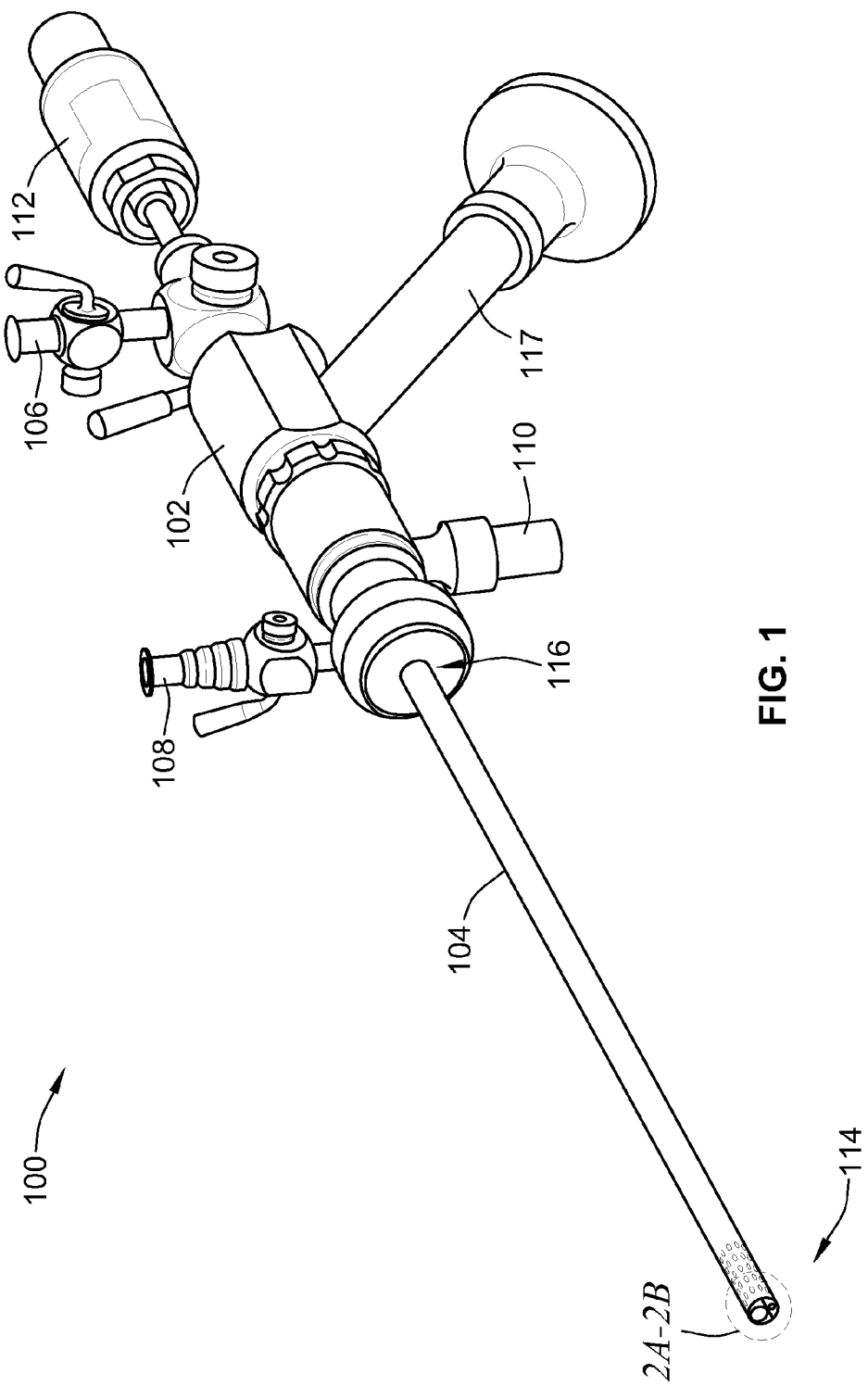
FIG. 1 is a perspective view of a hysteroscope system.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Referring to FIG. 1, a hysteroscope system 100 includes a hysteroscope 102 having, inter alia, a sheath 104, an inflow valve 106, an outflow valve 108, a light post 110, and a morcellator 112. The sheath 104 is a generally an elongated tubular member that has a distal end 114 and a proximal end 116. The hysteroscope system 100 also includes an arm 117 that is connected to an imaging device (e.g., a camera) to capture images received via a visualization device (e.g., visualization device 124).

According to some exemplary embodiments, the hysteroscope system 100 is intended for morcellation of uterine pathology with a scope and accessories having a sufficiently small diameter that can be inserted into a patient's uterus using the vaginoscopic approach. In particular, the hysteroscope system 100 provides a way to minimize patient pain because a tenanculum and speculum are not typically used.

Furthermore, anesthesia is not needed and the medical procedures can be performed in an office setting. This may result, for example, in a quicker surgery with less pain and quicker recovery, and may potentially lower the cost of the surgery. Yet another advantage of the hysteroscope system 100 is that a surgeon has the option to decide if they prefer greater flow instruments (e.g., with a coupled sheath 104) or smaller diameter instruments (e.g., with a removed sheath 104), depending on the patient case.

Figure 2A:
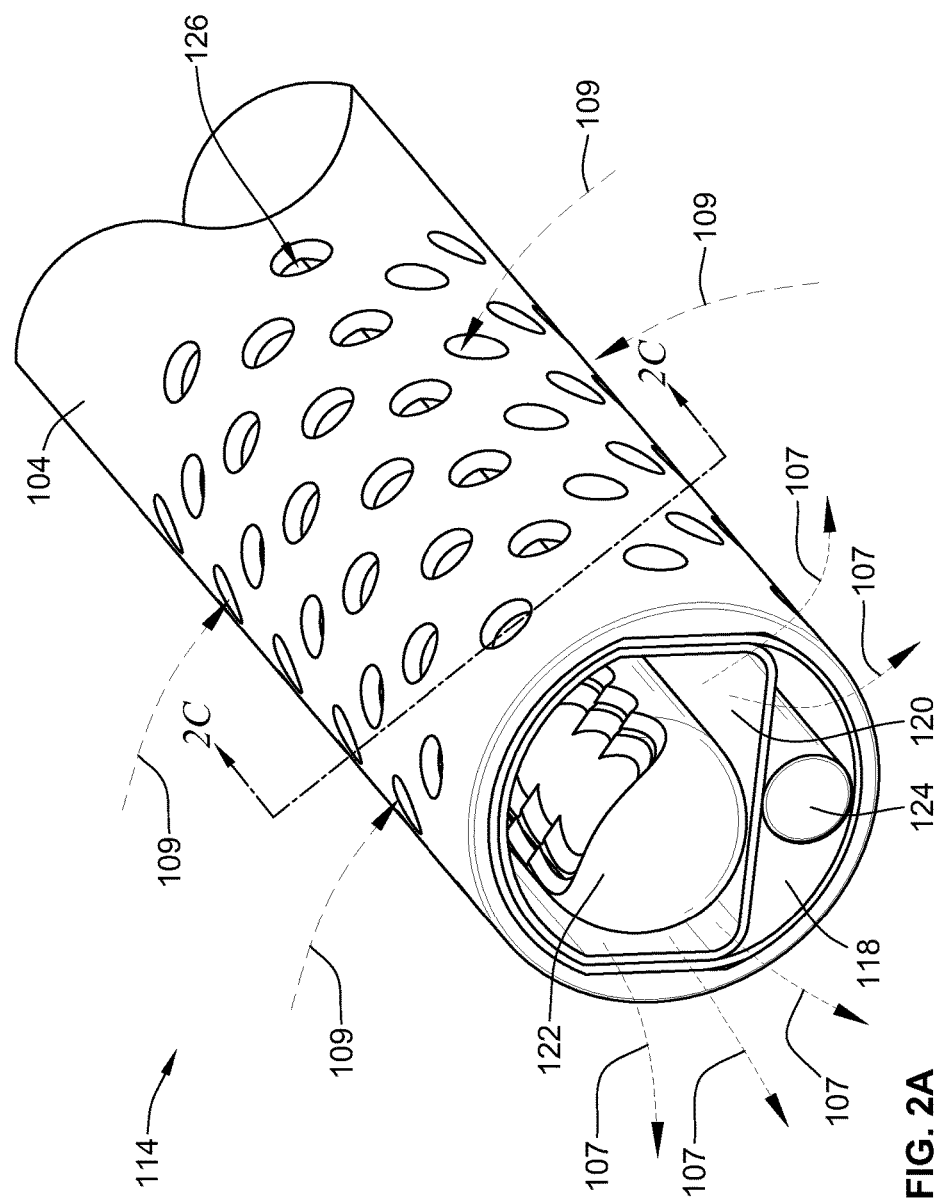
FIG. 2A is an enlarged perspective view of a distal end of the hysteroscope system.

Referring to FIG. 2A, the sheath 104 is removably coupled to a scope 118, which is generally an elongated tubular member having (similar to the sheath 104) a distal end 114 and a proximal end 116. More specifically, the sheath 104 is slidably fitted in an overlapping manner over the scope 118. The scope 118 includes an operative member 120, which is in the form of an elongated D-shape tubular member.

The operative member 120 receives internally a surgical tool 122, which can be selected from a variety of different tools. For example, the surgical tool 122 can be a rotary morcellator, a reciprocating morcellator, or a morcellator having both reciprocal and rotary capabilities. The scope 118 further includes a visualization device 124. The visualization device 124 is adjacent to the operative member 120 and can include various image devices. For example, the visualization device 124 can include fiber-optic technology for illumination and image transmission.

To maintain continuous outflow, a plurality of outflow holes 126 are formed near the distal end 114 of the sheath 104. The inflow valve 106 (shown in FIG. 1) regulates inflow of a liquid through the operative member 120, as represented by the arrows 107 extending from the operative member 120. The liquid is used, for example, to distend and irrigate the uterus of a patient. Furthermore, the liquid is generally received from an access pump, which delivers the fluid to produce a substantially constant predetermined pressure level within a joint cavity, e.g., a uterus. The outflow valve 108 (shown in FIG. 1) regulates outflow of the liquid through the outflow holes 126 via an outflow channel 128 (shown in FIG. 2C) formed between the sheath 104 and the scope 118. The outflow of the liquid is represented by the arrows 109 extending into the outflow holes 126. The outflow liquid is generally sent to a waste container.

Referring to FIG. 2B, the sheath 104 has at the distal end 114 a flange 130 extending inwardly towards the scope 118 to form a closed end of the outflow channel 128 (shown in FIG. 2C). The flange 130 has a generally oval shape and includes two pairs of opposite sides 130a-130d.

According to the illustrated embodiment, the shape of the flange 130 is non-uniform. For example, a second side 130b extends a greater distance internally towards the center of the scope 118 than a first side 130a. Similarly, based on the symmetric features of this embodiment, a fourth side 130d extends a greater distance internally towards the center of the scope 118 than a third side 130c. In alternative embodiments, the flange 130 can have different shapes and sizes.

Figure 2D:
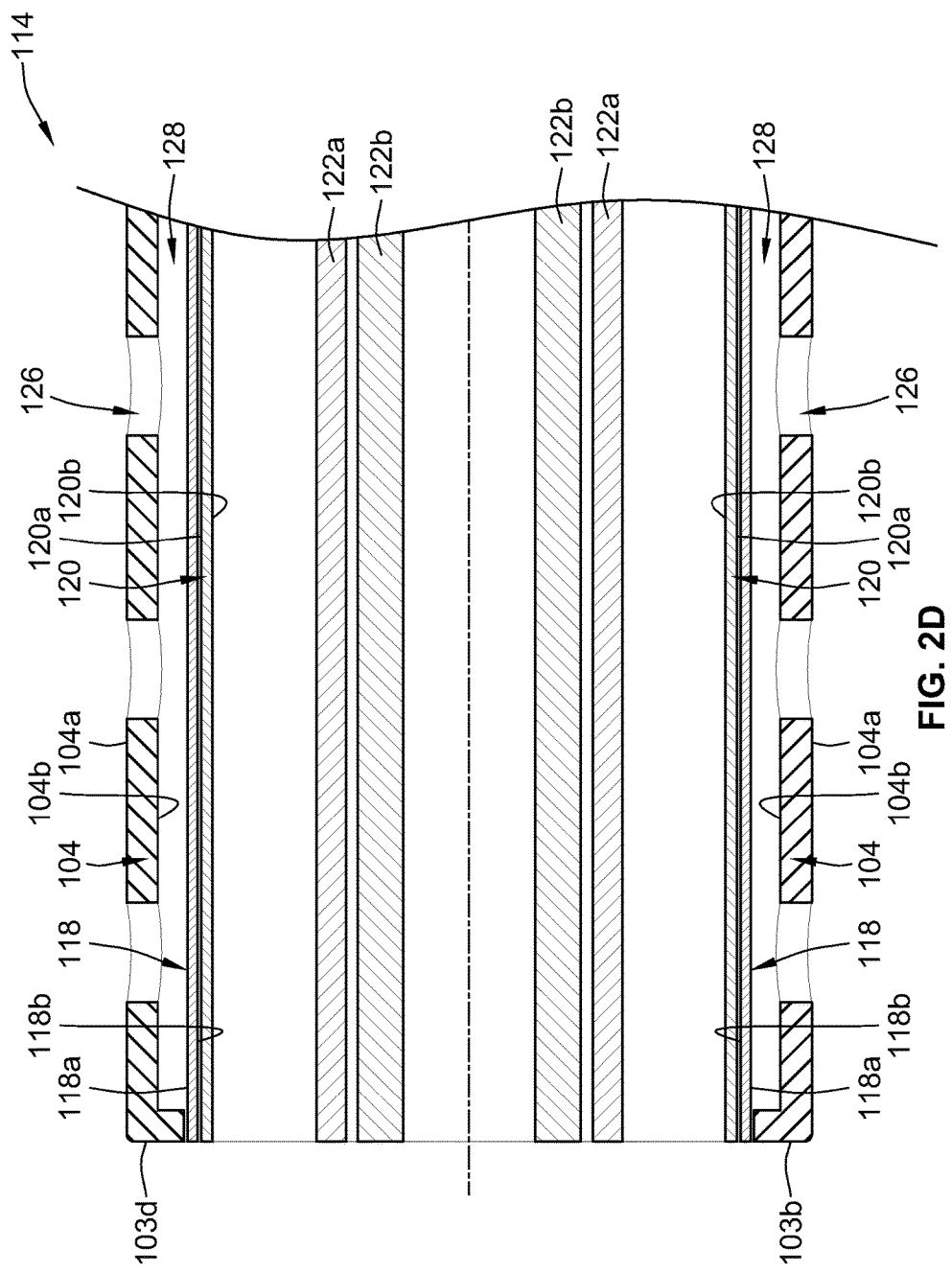
FIG. 2D is an enlarged cross-sectional top view of the distal end of the hysteroscope system.

Referring to FIGS. 2C-2D, the sheath 104 has an outer surface 104a and an internal surface 104b, and the scope 118 has an outer surface 118a and an internal surface 118b. The internal surface 104b of the sheath 104 defines an internal channel in which the scope 118 and the visualization device 124 are located. The internal surface 118b of the scope 118 defines an internal channel in which the outer member and thus the surgical tool 122 is located.

The operative member 120 has an outer surface 120a, an internal surface 120b, and a flat outer surface 120c (clearly shown in FIG. 2C). The flat outer surface 120c is spaced away from the internal surface 118b of the scope 118 to form a visualization channel 132 (clearly shown in FIG. 2C) in which the visualization device 124 is located. The visualization channel 132 is only a small part of the larger internal channel of the scope 118.

The outflow channel 128 is formed between the internal surface 104b of the sheath 104 and the outer surface 118a of the scope 118. An inflow channel 134 is formed in the internal channel of the scope 118. If the surgical tool 122 is removed, the inflow channel 134 is simply the entire internal channel of the scope 118. If the surgical tool 122 is in place, the inflow channel 134 is limited to the area between the surgical tool 122 and the internal surface 120b of the operative member 120.

Figure 3:
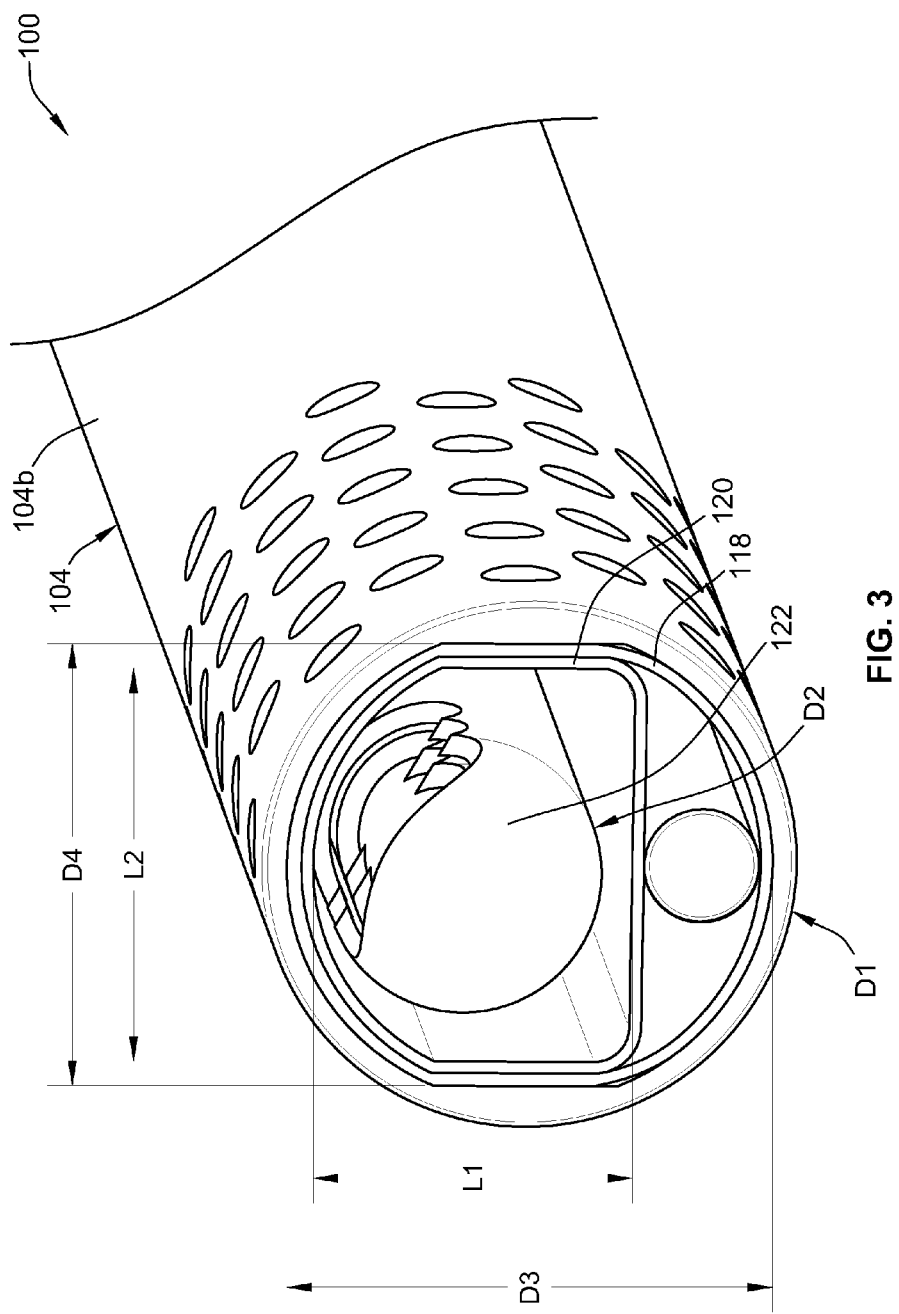
FIG. 3 shows dimensions associated with the distal end of FIG. 2A.

Referring to FIG. 3, the hysteroscopy system 100 is designed to have a size that can be used in an office setting. Specifically, the outer most diameter is designed to be about 6 millimeters or less. According to the illustrated embodiment, the outer diameter D1 of the sheath 104 (which is the same as the diameter of the outer surface 104b) is about 5.6 millimeters. For example, in an alternative embodiment the diameter of the sheath 104 is 5.5 millimeters. The outer diameter D2 of the surgical tool 122 (e.g., morcellator) is about 2.9 millimeters.

The scope 118 has an oval shape with a long diameter D3 of about 5.15 millimeters and a short diameter D4 of about 4.6 millimeters. The operative member 120 has a curvature dimension L1 of about 3.1 millimeters and a flat dimension L2 of about 3.95 millimeters.

The relatively small dimensions of the hysteroscopy system 100 allows a patient to be treated in an office setting. Generally, medical procedures may be provided to a patient with the use of the current hysteroscopy system 100 such that little or no anesthesia may be necessary. Clearly, one advantage of the hysteroscopy system 100 is that it is sufficiently small in diameter to be suitable for the vaginoscopic approach.

Figure 4:
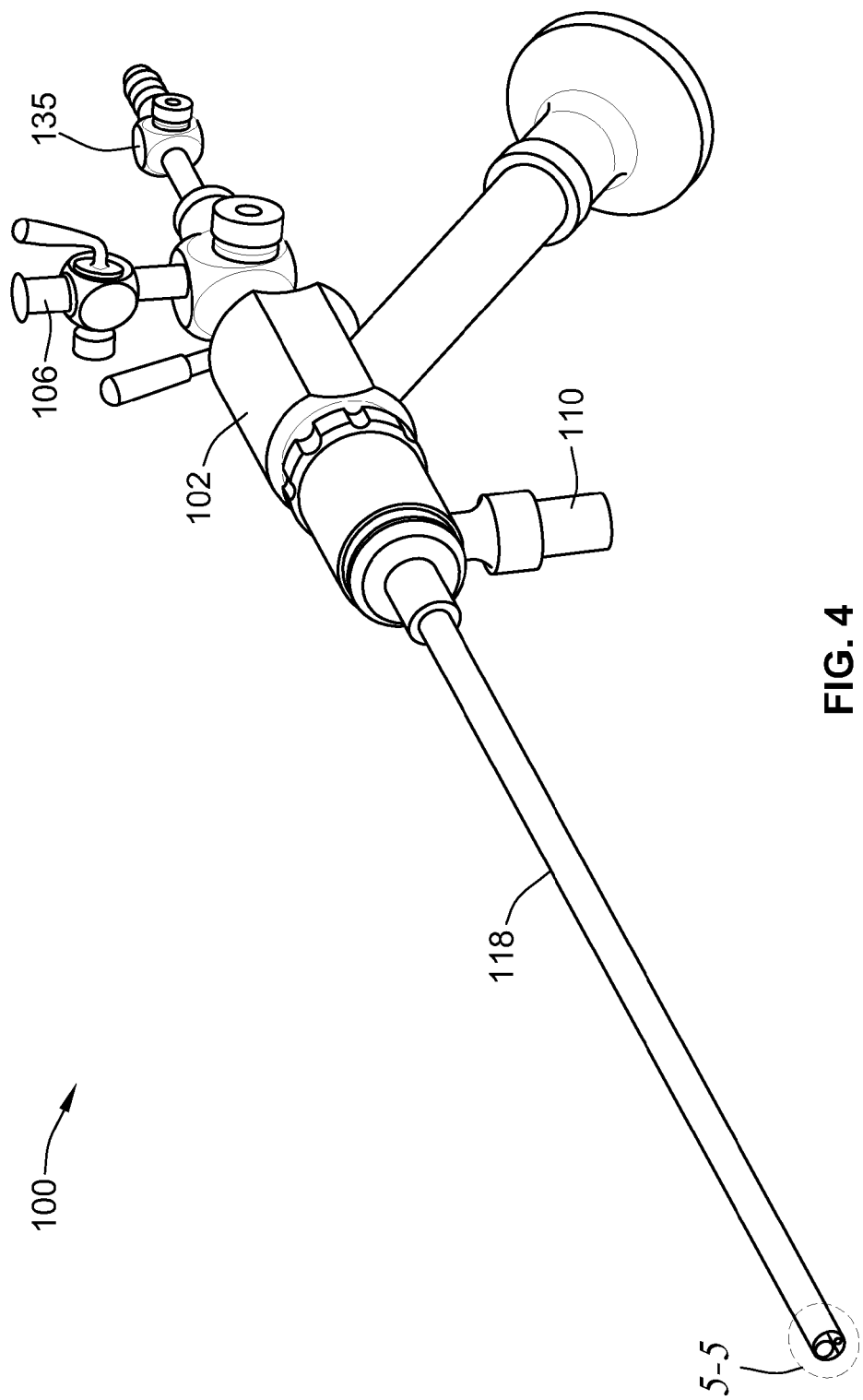
FIG. 4 is a perspective view of the hysteroscope system having a sheath removed from a scope.

Referring to FIG. 4, the hysteroscopy system 100 is also usable without the sheath 104 while still providing continuous flow via a diagnostic cannula 135 (e.g., a cannula having a diameter of about 2.9 millimeters). Specifically, the sheath 104 is removed to allow only the insertion of the scope 118 into a patient, e.g., into an uterus. The removal of the sheath 104 decreases the outermost diameter of the hysteroscopy system 100. For example, in accordance with the dimensions described above in reference to FIG. 3, the outermost diameter decreases to about 5.15 millimeters (the long diameter D3) from about 5.6 millimeters (the outer diameter D1). When the sheath 104 is removed, the outflow can be provided by an operation tool, such as the morcellator 112 described above (shown in FIGS. 1-3), or by the diagnostic cannula 135.

In contrast to previous scopes, the scope 118 does not have a flange extending outwards from its distal end. The outward extending flange of the previous scopes unnecessarily increased the outermost diameter of the respective scopes and created an obtrusive distal end that made it difficult, if not impossible, to introduce into a patient without a sheath and obturator.

Figure 5:
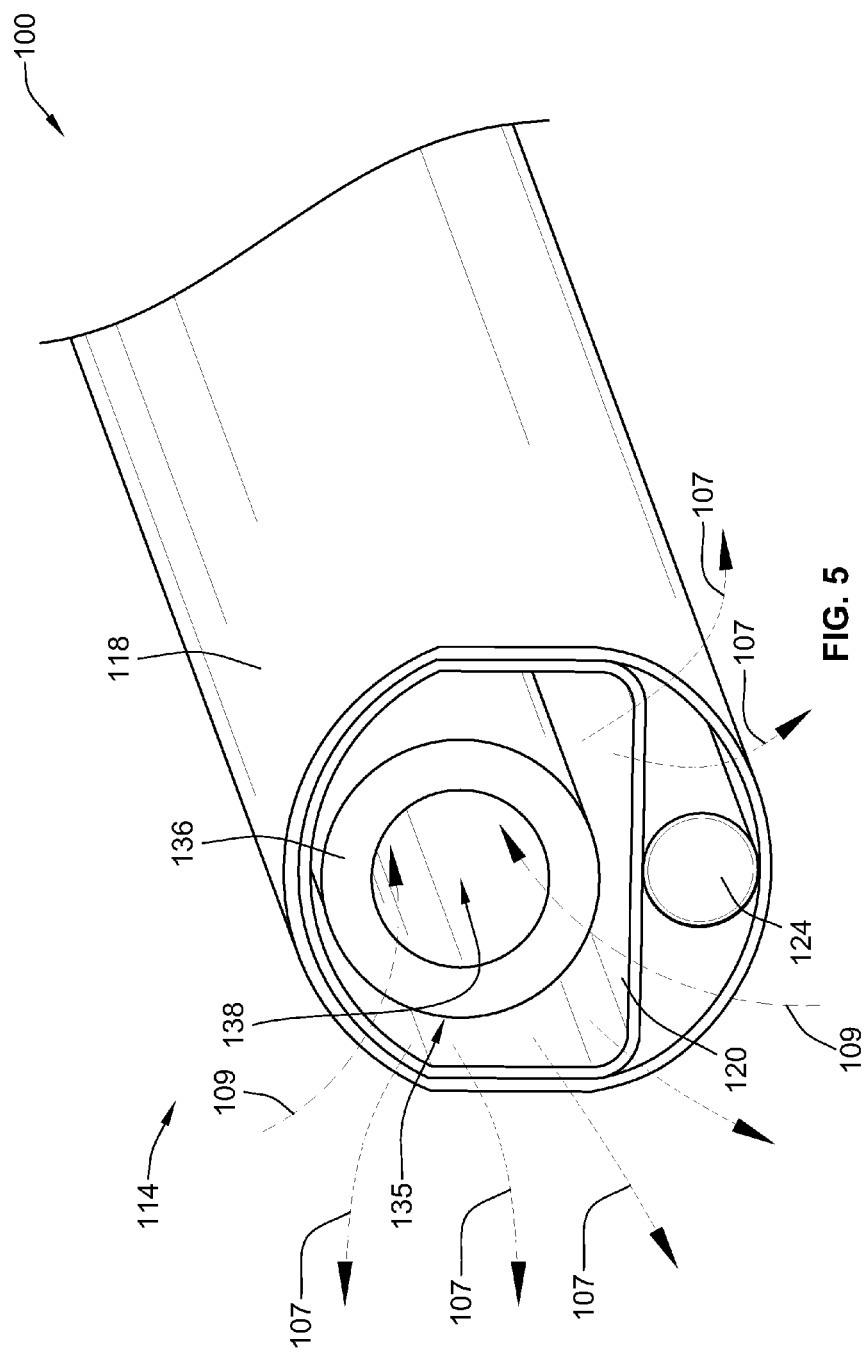
FIG. 5 is an enlarged perspective view of the distal end of the hysteroscope system of FIG. 4.

Referring to FIG. 5, the hysteroscopy system can be used for diagnostic purposes when the sheath 104 is removed. The sheath 104 is likely to be used in operative cases mostly to clear the visual field before introduction of a morcellator blade. The diagnostic cannula 135, which has a distal end 136, is used to create a smaller overall diameter of the system for diagnostic purposes. According to the dimensions described above, a reduction of approximately 0.5 millimeters can be achieved by removing the sheath 104. Another advantage of the cannula 135 is that it can be made reusable. Yet another advantage of the cannula 135 is that it can be used to distend and irrigate the patient's uterus during the diagnostic procedure.

The cannula 135 allows for continuous outflow but does not extend beyond the distal end of the scope 118. For example, the cannula 135 provides a replacement for the outflow channel 128, which is removed with the removal of the sheath 104. Specifically, the cannula 135 provides an alternative outflow channel 138 to replace the outflow channel 128 formed by the sheath 104. As such, continuous flow can be maintained even if the sheath 104 is removed.

Figure 6:
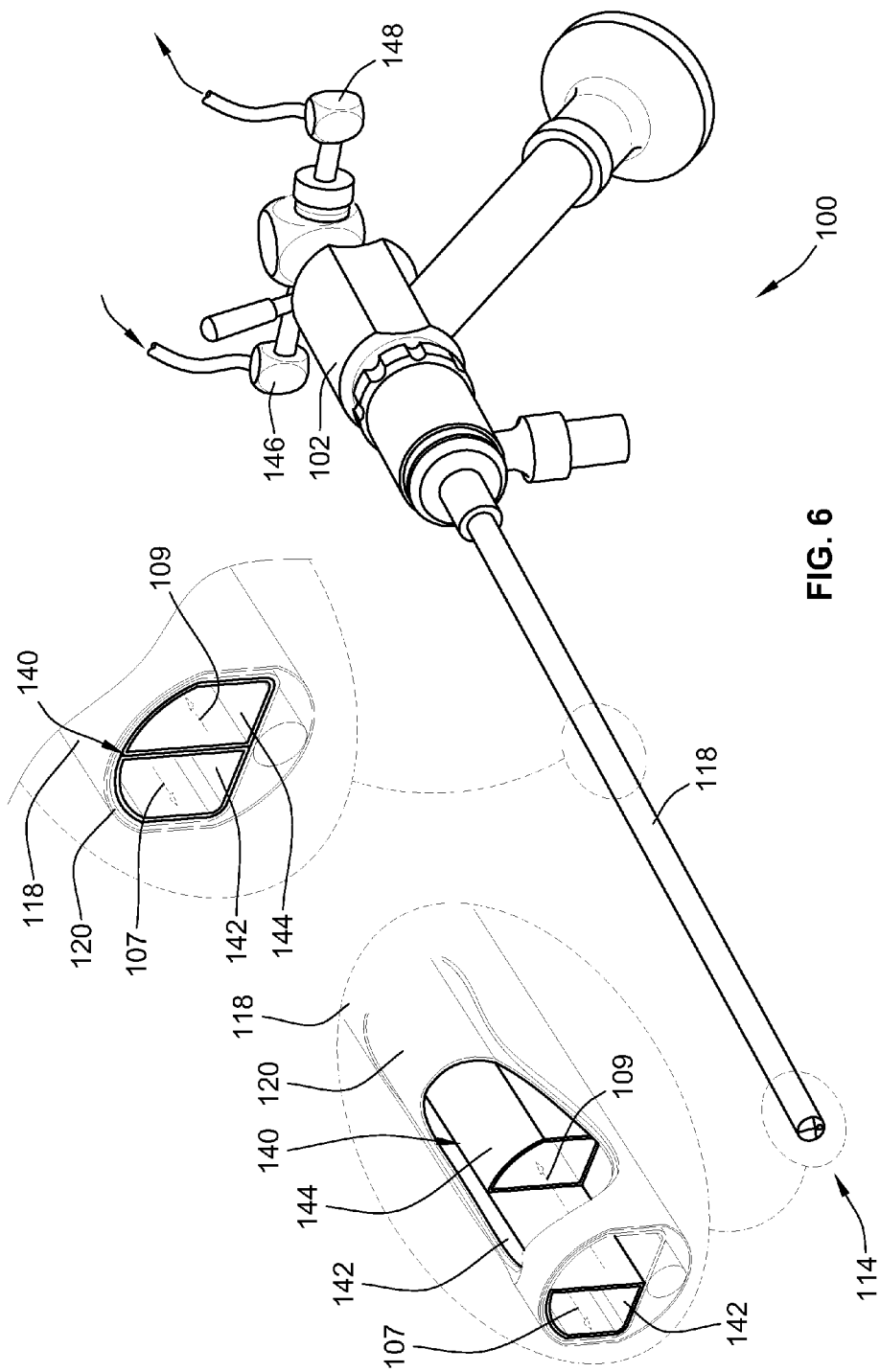
FIG. 6 is a perspective view of an alternative embodiment of the hysteroscope system.

Referring to FIG. 6, the hysteroscope system 100 alternatively includes a flow device 140 inserted within the operative member 120. The flow device 140 has an inflow tubular element 142 and an outflow tubular element 144, which can be conjoined elements or separate elements.

The distal ends of the tubular elements 142, 144 terminate at different points within the operative member 120. Preferably, the distal end of the inflow tubular element 142 terminates at the distal end 114 of the scope 118, and the distal end of the outflow tubular element 144 terminates some distance away from the distal end 114 within the operative member 120. The termination of tubular elements 142, 144 at different points along the operative member 120 eliminates the possibility of fluid short-circuit and provides better circulation and, hence, irrigation within the uterus.

According to one example, the flow device 140 is made of stainless steel and, as such, can be a reusable device. According to another example, the flow device 140 is made from a much more cost-effective material, such as a polymer. If a polymer is used, the flow device 140 will typically be considered a single-use device.

In practice, for example, a surgeon will insert the flow device 140 into the operative member 120 of the hysteroscope 102 prior to introduction into the uterus of a patient. After hysteroscope introduction into the uterus, an inflow valve 146 of the flow device 140 will be opened and the uterus will be distended. Then, by opening an outflow valve 148 of the flow device 140, irrigation is achieved. In the case of a diagnostic procedure, the flow device 140 could stay in place for the duration of the surgery. In the case of an operative procedure, the flow device 140 is removed and an operative tool (e.g., the morcellator 112) is inserted into the scope 118.

While the best modes for carrying out the present invention have been described in detail, those familiar with the art to which this invention relates will recognize various alternative designs and embodiments for practicing the invention within the scope of the appended claims. For example, the sheath 104, the scope 118, and the surgical tool 122 can be circular, oval, or any other smooth shape (i.e., an unobtrusive shape such as a shape that does not have a outward extending flange). In another example, the operative member 120 can have a circular shape or any other similar shape to the illustrated D-shape.

What is claimed is:

1. A hysteroscopy system comprising:
   a scope having an outer surface and an inner surface, the outer surface having a uniform cross section along a length of the scope;
   an operative member within the scope having an outer surface and an inner surface, the inner surface defining an operative channel, and at least part of the outer surface of the operative member and the inner surface of the scope defining a visualization channel; and
   a sheath removably coupled to and surrounding the scope, the sheath including a tube defining a longitudinal axis, a distal end of the tube being in a shape of a flange extending perpendicular relative to the longitudinal axis towards the outer surface of the scope, wherein the outer surface of the scope and an inner surface of the tube form an outflow channel, and the flange abuts the outer surface of the scope to form an end of the outflow channel.

2. The hysteroscopy system of claim 1, wherein a radial cross section of the outer surface of the scope at a distal end of the scope forms a shape with flat symmetrical sides between arcuate symmetrical sides.

3. The hysteropscopy system of claim 1, wherein the visualization channel is configured to receive a visualization device.

4. The hysteroscopy system of claim 1, wherein an outer diameter of the sheath is about 5.6 millimeters.

5. The hysteroscopy system of claim 4, wherein an outer diameter of the scope is about 4.6 to 5.15 millimeters.

6. The hysteroscopy system of claim 1, wherein a radial cross section of the operative member forms a horizontal D-shape.

7. The hysteroscopy system of claim 1, further comprising a surgical tool within the operative channel.

* * * * *